United States Patent [19]

Uno et al.

[11] 4,356,186

[45] Oct. 26, 1982

[54] ACETIC ACID DERIVATIVES AND COMPOSITION CONTAINING THE SAME

[75] Inventors: Hitoshi Uno, Takatsuki; Mikio Kurokawa, Kobe; Hideo Nakamura, Tenri, all of Japan

[73] Assignee: Dainippon Pharmaceutical Co., Ltd., Japan

[21] Appl. No.: 246,114

[22] Filed: Mar. 20, 1981

[30] Foreign Application Priority Data

Mar. 31, 1980 [JP]  Japan .................. 55/42167

[51] Int. Cl.³ .................. A61K 31/335; A61K 31/38; C07D 313/12; C07D 337/12
[52] U.S. Cl. .................. 424/275; 424/248.51; 424/248.54; 424/248.57; 424/250; 424/251; 424/258; 424/263; 424/267; 424/274; 424/278; 424/285; 544/145; 544/147; 544/298; 544/318; 544/319; 544/375; 546/141; 546/147; 546/153; 546/174; 546/196; 546/202; 546/269; 546/274; 548/525; 549/12; 549/354
[58] Field of Search .................. 260/326.35, 326.36, 260/326.5 SA, 326.5 CA, 333, 347.4; 424/248.51, 248.54, 248.57, 250, 251, 258, 263, 267, 274, 275, 278, 285; 544/145, 147, 298, 318, 319, 375; 546/141, 147, 153, 174, 196, 202, 269, 274; 549/12, 354

[56] References Cited

U.S. PATENT DOCUMENTS 4,000,308  12/1976  Ackrell .................. 549/12 X
4,107,322  8/1978  McFadden et al. .................. 260/333 X

FOREIGN PATENT DOCUMENTS 1476214  6/1977  United Kingdom .
1476215  6/1977  United Kingdom .
1481866  8/1977  United Kingdom .

OTHER PUBLICATIONS

Kirby et al., J.C.S. Chem. Comm., 1980, No. 4, pp. 150 and 151.

*Primary Examiner*—Richard Raymond

*Attorney, Agent, or Firm*—Stevens, Davis, Miller & Mosher

[57] ABSTRACT

Novel acetic acid derivatives of the formula:

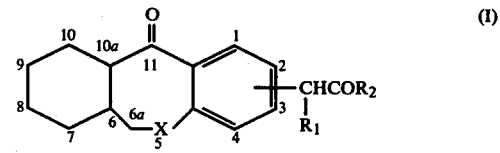

(I)

wherein X is oxygen or sulfur; $R_1$ is hydrogen or a lower alkyl; $R_2$ is hydroxy, an alkoxy, an alkenyloxy, a cycloalkyloxy, an aryloxy, a substituted aryloxy, an aryl-lower alkoxy, a substituted aryl-lower alkoxy, an aryl-lower alkenyloxy, a substituted aryl-lower alkenyloxy, an ω-disubstituted amino-lower alkoxy, a lower alkoxycrbonyl-lower alkoxy, a lower alkoxy-lower alkoxy, a hydroxy-lower alkoxy-lower alkoxy, an acyl-lower alkoxy, or a group

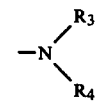

wherein $R_3$ is hydrogen, hydroxy, a lower alkyl, an aryl-lower alkyl, a hydroxy-lower alkyl, or a carboxy-lower alkyl, $R_4$ is hydrogen, a lower alkyl or a hydroxy-lower alkyl, or the $R_3$ and $R_4$ may combine together with the nitrogen atom to which they are joined to form a heterocyclic group; and the group $-CH(R_1)COR_2$ is joined to the carbon atom at 2- or 3-position, and pharmaceutically acceptable salts thereof, processes for their preparation, and pharmaceutical compositions containing these compounds. They have excellent anti-inflammatory, analgesic and antipyretic activities with weak ulcerogenicity in the gastrointestinal tract and toxicity.

22 Claims, 1 Drawing Figure

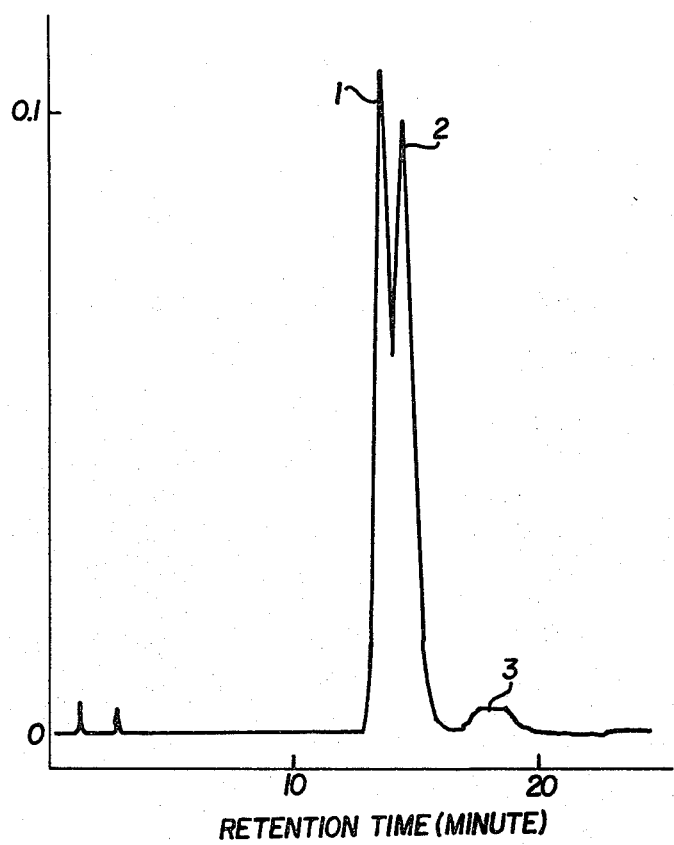

ACETIC ACID DERIVATIVES AND COMPOSITION CONTAINING THE SAME

The present invention relates to novel acetic acid derivatives having anti-inflammatory, analgesic and antipyretic properties. More particularly, it relates to 6,6a,7,8,9,10,10a,11-octahydro-11-oxo-dibenz[b,e]oxepin-acetic acid derivatives and 6,6a,7,8,9,10,10a,11-octahydro-11-oxodibenzo[b,e,]thiepin-acetic acid derivatives, and pharmaceutically acceptable salts thereof, process for the preparation thereof, and pharmaceutical composition containing these compounds as an active ingredient.

There has scarcely been known a compound having 6,6a,7,8,9,10,10a,11-octahydro-11-oxodibenz[b,e]oxepin ring or 6,6a,7,8,9,10,10a,11-octahydro-11-oxodibenzo[b,e]thiepin ring. To the inventors' knowledge, it is merely reported that 6,6a,7,8,9,10,10a,11-octahydro-11-oxodibenzo[b,e]thiepin-5,5-dioxide is synthesized by irradiation of 3-acetoxybenzo[b]thiophen 1,1-dioxide in the presence of cycloalkenes, followed by treatment with methanolic sodium hydroxide (J. Chem. Soc. Chem. Comm., 1980, No. 4, 150). However, this compound is dioxide and has no substituent such as an alkanoic acid group and hence, it is clearly different from the compounds of this invention in the chemical structure, and further, any pharmacological property thereof is not mentioned. Besides, it is described in British Pat. Nos. 1,476,214, 1,476,215 and 1,481,866, U.S. Pat. No. 4,107,322, etc. that some dibenz[b,e]oxepin-acetic acid derivatives show anti-inflammatory and analgesic properties. It is also described in U.S. Pat. No. 4,000,308, etc. that some dibenzo[b,e]thiepin-acetic acid derivatives show anti-inflammatory property. These known compounds are, however, clearly different from the compounds of this invention in the chemical structure.

The compounds of the present invention are acetic acid derivatives of the following general formula (I):

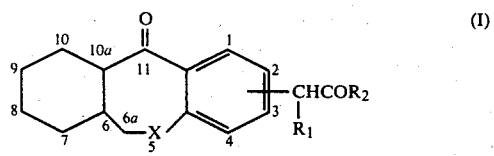

wherein X is oxygen or sulfur; $R_1$ is hydrogen or a lower alkyl; $R_2$ is hydroxy, an alkoxy, an alkenyloxy, a cycloalkyloxy, an aryloxy, a substituted aryloxy, an aryl-lower alkoxy, a substituted aryl-lower alkoxy, an aryl-lower alkenyloxy, a substituted aryl-lower alkenyloxy, an ω-disubstituted amino-lower alkoxy, a lower alkoxycarbonyl-lower alkoxy, a lower alkoxy-lower alkoxy, a hydroxy-lower alkoxy-lower alkoxy, an acyl-lower alkoxy, or a group

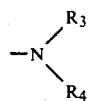

wherein $R_3$ is hydrogen, hydroxy, a lower alkyl, an aryl-lower alkyl, a hydroxy-lower alkyl, or a carboxy-lower alkyl, $R_4$ is hydrogen, a lower alkyl or a hydroxy-lower alkyl, or the $R_3$ and $R_4$ may combine together with the nitrogen atom to which they are joined to form a heterocyclic group; and the group $-CH(R_1)COR_2$ is joined to the carbon atom at 2- or 3-position, and pharmaceutically acceptable salts thereof.

The pharmaceutically acceptable salts include salts of the compounds (I) wherein $R_2$ is hydroxy with an inorganic or organic base, and salts of the compounds (I) wherein $R_2$ is a basic group with an inorganic or organic acid. The salts with an inorganic base include sodium, potassium, calcium, magnesium, aluminum, ammonium salt, or the like. The salts with an organic base include salts of organic amines such as isopropylamine, diethylamine, ethanolamine, piperidine, or the like. The salts of an inorganic acid include hydrochloride, hydrobromide, hydriodide, sulfate, phosphate, or the like, and the salts of an organic acid include methanesulfonate, maleate, fumarate, or the like.

The compounds (I) of the present invention contain two adjacent asymmetric carbon atoms (at 6a and 10a positions), and hence, two trans isomers and two cis isomers exist. Moreover, in the compounds (I) wherein $R_1$ is lower alkyl, the carbon atom to which $R_1$ is joined is also asymmetric and totally eight stereo-isomers exist. The present invention includes these stereo-isomers, a mixture thereof, and also racemic mixtures.

In the present specification, the term "lower" means that a group qualified by this term has up to 4 carbon atoms. "Alkoxy" denotes a straight or branched alkoxy having 1 to 12 carbon atoms, preferably 1 to 6 carbon atoms, and includes, for example, methoxy, ethoxy, propoxy, isopropoxy, butoxy, isobutoxy, sec-butoxy, pentyloxy, isopentyloxy, and hexyloxy. "Alkenyloxy" denotes a straight or branched alkenyloxy having 3 to 11 carbon atoms, preferably 3 to 5 carbon atoms, and includes, for example, allyloxy, 3-butenyloxy, 1-methyl-2-butenyloxy, 1-methyl-3-butenyloxy, and 4-pentenyloxy. "Cycloalkyloxy" denotes a cycloalkyloxy having 4 to 8 carbon atoms, and includes, for example, cyclobutyloxy, cyclopentyloxy, cyclohexyloxy, and cycloheptyloxy.

"Aryl" denotes an aromatic hydrocarbon group, such as phenyl or naphthyl, and an aromatic heterocyclic group, such as furyl, thienyl, pyridyl, quinolyl, isoquinolyl, or pyrimidinyl, among which phenyl and pyridyl are preferable. "Substituted aryl" denotes an aryl substituted with a halogen (e.g. fluorine, chlorine, or bromine), a lower alkyl (e.g. methyl) or a lower alkoxy (e.g. methoxy). "Aryl-lower alkoxy" denotes an alkoxy having 1 to 4 carbon atoms which is substituted with an aryl, and includes, for example, benzyloxy, phenethyloxy, β-methylphenethyloxy, 3-phenylpropoxy, 2-furfuryloxy, 2-thienylmethoxy, 2-pyridylmethoxy, 2-(2-pyridyl)ethoxy, 3-pyridylmethoxy, 2-(3-pyridyl)ethoxy, 4-pyridylmethoxy, 2-(4-pyridyl)ethoxy, or the like. "Aryl-lower alkenyloxy" and "substituted aryl-lower alkenyloxy" denote an alkenyloxy having 3 to 4 carbon atoms which is substituted with an aryl or a substituted aryl, and include, for example, cinnamyloxy, p-methylcinnamyloxy, and 3-(2-pyridyl)allyloxy.

"ω-Disubstituted amino-lower alkoxy" denotes an alkoxy having 2 to 4 carbon atoms which has a disubstituted amino group at the terminal carbon atom, wherein the disubstituted amino denotes an amino substituted with two alkyl having 1 to 3 carbon atoms or a 5- or 6-membered cyclic amino, and includes, for example, 2-dimethylaminoethoxy, 2-diethylaminoethoxy, 2-(1-pyrrolidinyl)ethoxy, 2-piperidinoethoxy, 2-morpholinoethoxy, and 2-(4-methyl-1-piperazinyl)ethoxy. "Lower alkoxycarbonyl-lower alkoxy" denotes an alkoxy having 1 to 4 carbon atoms which is substituted with an alkoxycarbonyl having 2 to 5 carbon atoms, and includes, for example, methoxycarbonylmethoxy, ethoxycarbonylmethoxy, 2-methoxycarbonylethoxy, and 2-ethoxycarbonylethoxy. "Lower alkoxy-lower alkoxy" denotes an alkoxy having 2 to 4 carbon atoms which is substituted with an alkoxy having 1 to 4 carbon atoms, and includes, for example, 2-methoxyethoxy, 2-ethoxyethoxy, 3-methoxypropoxy, and 3-ethoxypropoxy. "Hydroxy-lower alkoxy-lower alkoxy" denotes an alkoxy having 2 to 4 carbon atoms which is substituted with an alkoxy having 2 to 4 carbon atoms and being substituted with one or two hydroxy groups, and includes, for example, 2-(2-hydroxyethoxy)ethoxy and 2-(2,3-dihydroxypropoxy)ethoxy. "Acyl-lower alkoxy" denotes an alkoxy having 1 to 4 carbon atoms which is substituted with a straight or branched alkanoyl having 1 to 6 carbon atoms or an arylcarbonyl, and includes, for example, formylmethoxy, acetonyloxy, 2-formylethoxy, 3-formylpropoxy, and phenacyloxy.

"Hydroxy-lower alkyl" denotes an alkyl having 2 to 4 carbon atoms which is substituted with hydroxy, and includes, for example, 2-hydroxyethyl and 3-hydroxypropyl. "Carboxy-lower alkyl" denotes an alkyl having 1 to 4 carbon atoms which is substituted with carboxy, and includes, for example, carboxymethyl, 1-carboxyethyl, and 2-carboxyethyl.

The term "heterocyclic group" which is formed by combining the $R_3$ and $R_4$ groups together with the nitrogen atom to which they are joined denotes a 5- or 6-membered heterocyclic group which may contain additional one hetero atom selected from nitrogen, oxygen and sulfur, said heterocyclic group being optionally substituted with a lower alkyl or a hydroxy-lower alkyl, and includes, for example, 1-pyrrolidinyl, piperidino, morpholino, 4-methyl-1-piperazinyl, and 4-(2-hydroxyethyl)-1-piperazinyl.

Preferable compounds of the present invention are the compounds (I) wherein $R_1$ is hydrogen or methyl (methyl is more preferable), and the group —CH($R_1$)COR$_2$ is bonded to the carbon atom at 3-position.

Particularly preferable compounds are the compounds of the formula (II):

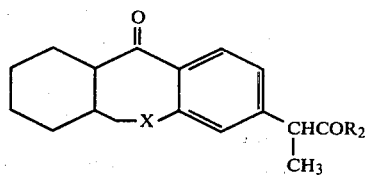

wherein X is as defined above; and $R_2$ is hydroxy, an alkoxy having 1 to 6 carbon atoms, an alkenyloxy having 3 to 5 carbon atoms, cyclohexyloxy, phenyloxy, a phenyl-lower alkoxy, a pyridyl-lower alkoxy, a phenyl-lower alkenyloxy, an ω-disubstituted amino-lower alkoxy, a lower alkoxycarbonyl-lower alkoxy, a lower alkoxy-lower alkoxy, a hydroxy-lower alkoxy-lower alkoxy, a benzoyl-lower alkoxy, amino, hydroxyamino, a hydroxy-lower alkylamino, or a carboxy-lower alkylamino. Among the compounds (II), the compounds wherein $R_2$ is hydroxy, an alkoxy having 1 to 4 carbon atoms, phenethyloxy, 2-pyridylmethoxy, 2-(2-pyridyl)ethoxy or amino are especially preferable.

The compounds (I) wherein $R_2$ is hydroxy or a lower alkoxy can be prepared, for example, by subjecting a compound of the formula (III):

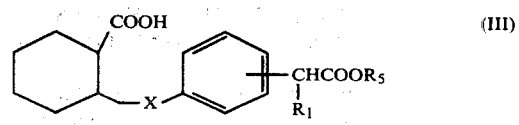

wherein X and $R_1$ are as defined above, and $R_5$ is hydrogen or a lower alkyl, to cyclization reaction, optionally followed by hydrolysis.

The cyclization of the compound (III) can be carried out, for example, by directly cyclizing the compound (III) in the presence of a condensing agent, or by converting the compound (III) into an acid halide compound thereof with a halogenating agent such as thionyl chloride or phosphorus trichloride and then subjecting the acid halide compound to Friedel-Crafts reaction.

The condensing agent used in the direct cyclization includes all conventional condensing agents which are usually applicable to intramolecular acylation reaction, for example, polyphosphoric acid, a polyphosphate ester, trifluoroacetic anhydride, phosphoryl chloride-zinc chloride, phosphorus pentoxide, or the like. This direct cyclization reaction is usually carried out by heating the compound (III) at a temperature of from about 50° to about 150° C., preferably from about 80° to about 120° C. for a period of time of from about 30 minutes to about 8 hours, preferably from about 30 minutes to about 5 hours in the absence of a solvent or in an appropriate inert solvent such as benzene, toluene or xylene. When polyphosphoric acid or a polyphosphate ester is used as the condensing agent, it can also be used as the solvent by using in an excess amount.

The cyclization of the acid halide of the compound (III) by Friedel-Crafts reaction can be carried out in a usual manner. For example, the reaction is usually carried out in an aprotic inert solvent such as dichloromethane, carbon disulfide or the like in the presence of a known Lewis acid catalyst such as aluminum chloride, zinc chloride or the like at a temperature of from about −20° to about 40° C. for a period of time of from about 5 minutes to about 8 hours. When the compound (III) wherein $R_5$ is hydrogen is cyclized by this Friedel-Crafts reaction, the cyclized product is obtained in the form of an acid halide compound. This acid halide compound can be converted into the compound (I) wherein $R_2$ is hydroxy (i.e. the compound (Ia) as mentioned hereinafter) by subjecting the acid halide compound to hydrolysis in a usual manner, for example, by contacting it with an aqueous solution of a base (e.g. sodium hydroxide, potassium hydroxide, sodium carbonate, potassium carbonate).

When a compound of the formula (I) wherein $R_2$ is a lower alkoxy is obtained in the above cyclization, this compound can be converted into the compound (Ia) by hydrolyzing it in a usual manner. For example, the conversion can be carried out by contacting the compound with water or an aqueous lower alcohol (e.g. ethanol, isopropanol) in the presence of a base (e.g. sodium hydroxide, potassium hydroxide, sodium carbonate, potassium carbonate) or an acid (e.g. hydrochloric acid, sulfuric acid, hydrobromic acid) at a temperature of from room temperature to about 100° C. for a period of time of from about 10 minutes to about 5 hours.

The compounds (I) wherein $R_2$ is a group other than hydroxy can be prepared by subjecting a carboxylic acid compound of the formula (Ia) obtained in the above cyclization reaction or a reactive derivative thereof to esterification or amidation in a usual manner.

For example, a compound of the formula (I) wherein $R_2$ is a group other than hydroxy and a group

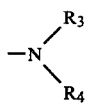

can be prepared by reacting a carboxylic acid compound of the formula (Ia):

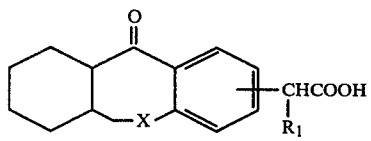

wherein X and $R_1$ are as defined above, or a reactive derivative thereof with a compound of the formula (IV):

$$Z-R_6 \quad (IV)$$

wherein Z is hydroxy or a residue of a reactive ester of an alcohol, and $R_6$ is an alkyl, an alkenyl, a cycloalkyl, an aryl, a substituted aryl, an aryl-lower alkyl, a substituted aryl-lower alkyl, an aryl-lower alkenyl, a substituted aryl-lower alkenyl, an ω-disubstituted amino-lower alkyl, a lower alkoxycarbonyl-lower alkyl, a lower alkoxy-lower alkyl, a hydroxy-lower alkoxy-lower alkyl, or an acyl-lower alkyl.

The reactive derivative of the carboxylic acid compound (Ia) includes a metal salt, especially an alkali metal salt of the compound (Ia) (e.g. sodium salt, potassium salt), and a halide, a mixed acid anhydride or a lower alkyl ester of the compound (Ia). The residue of a reactive ester of an alcohol as defined for the Z group includes, for example, a halogen atom (e.g. chlorine, bromine, iodine), an organic sulfonyloxy group (e.g. benzenesulfonyloxy, p-toluenesulfonyloxy, methanesulfonyloxy), or the like.

The metal salt of the compound (Ia) reacts with a compound (IV) wherein Z is a residue of a reactive ester of an alcohol, and the compound (Ia) or the other reactive derivatives of the compound (Ia) react with a compound (IV) wherein Z is hydroxy. These reactions can be carried out under the same conditions as used in a conventional esterification reaction.

For example, the reaction of a metal salt of the compound (Ia) with the compound (IV) wherein Z is a residue of a reactive ester of an alcohol is usually carried out in an appropriate solvent (e.g. benzene, toluene, xylene, dimethylformamide) at a temperature of from about 50° to about 150° C. for a period of time of from about 2 to about 20 hours.

The reaction of the carboxylic acid compound (Ia) with the compound (IV) wherein Z is hydroxy is usually carried out in the absence of a solvent or in an appropriate solvent (e.g. benzene, toluene, xylene, dichloroethane, tetrahydrofuran, dioxane) in the presence of an acid (e.g. sulfuric acid, hydrogen chloride, ferric chloride, boron trifluoride, p-toluenesulfonic acid) at a temperature of from about 50° to about 150° C. for a period of time of from about 30 minutes to about 40 hours.

The halide of the carboxylic acid compound (Ia) can be prepared by reacting the carboxylic acid compound (Ia) with a halogenating agent (e.g. thionyl chloride, phosphorus trichloride) in a usual manner. The reaction of the halide with the compound (IV) wherein Z is hydroxy is usually carried out in an appropriate solvent (e.g. benzene, toluene, xylene, chloroform, tetrahydrofuran, dioxane, acetone, ethyl acetate, water), optionally in the presence of an acid acceptor such as an organic base (e.g. pyridine, dimethylaniline, triethylamine), an inorganic base (e.g. an alkali metal bicarbonate, an alkali metal carbonate, an alkali metal hydroxide), or magnesium. This reaction is usually carried out at a temperature of from about 0° to about 150° C. for a period of time of from about 30 minutes to about 20 hours.

The mixed acid anhydride of the carboxylic acid compound (Ia) can be prepared by reacting the carboxylic acid compound (Ia) with a reagent such as trifluoroacetic anhydride, benzenesulfonyl chloride, p-toluenesulfonyl chloride, a lower alkyl chlorocarbonate or the like in a usual manner. The reaction of the mixed acid anhydride with the compound (IV) wherein Z is hydroxy is usually carried out in an appropriate solvent (e.g. benzene, chloroform, dichloromethane, dioxane, pyridine) at a temperature of from about 0° to about 120° C. for a period of time of from about 30 minutes to about 20 hours.

The reaction of the lower alkyl ester of the carboxylic acid compound (Ia) with the compound (IV) wherein Z is hydroxy can be carried out under the same conditions as used in the conventional transesterification reaction.

For the preparation of the compounds (I) wherein $R_2$ is an aryloxy or a substituted aryloxy, the processes using the halide or mixed acid anhydride of the carboxylic acid compound (Ia) are preferable. On the other hand, in the preparation of the compounds (I) wherein $R_2$ is a hydroxy-lower alkoxy-lower alkoxy and the alcohol moiety is not symmetric, the process using a metal salt of the carboxylic acid compound (Ia) is preferable.

The compounds (I) wherein $R_2$ is a group

can be prepared by reacting a carboxylic acid compound of the formula (Ia) or a reactive derivative thereof with a compound of the formula (V):

 (V)

wherein $R_3$ and $R_4$ are as defined above.

The reactive derivative of the carboxylic acid compound (Ia) includes a halide of the carboxylic acid compound (Ia) and a mixed acid anhydride thereof with a lower alkylcarbonic acid (e.g. ethylcarbonic acid). The reaction of the carboxylic acid compound (Ia) or a reactive derivative thereof with the compound (v) can be carried out under the same conditions as used in the conventional amidation reaction. For example, the reaction of the halide with the compound (V) is usually carried out in an appropriate solvent as used in the esterification reaction as mentioned hereinbefore, preferably in the presence of an acid acceptor such as an organic base, an alkali metal bicarbonate, an alkali metal carbonate, or an alkali metal hydroxide as mentioned hereinbefore. The compound (V) may also be used as can be converted into a salt thereof with an inorganic or organic acid by treating the compounds (I) with the inorganic or organic acid in a usual manner.

The starting compounds (III) are novel compounds and can be prepared, for example, by the process as shown in the following reaction scheme:

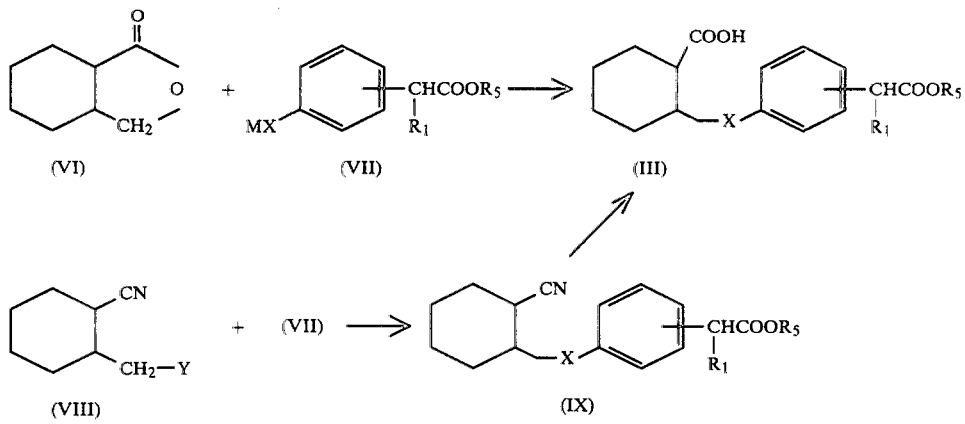

the acid acceptor when used in an excess amount. This reaction is usually carried out at a temperature of from about 0° to about 80° C. for a period of time of from about 10 minutes to about 5 hours.

The compound (I) obtained by the above processes can easily be isolated and purified in a usual manner.

According to the processes as mentioned above, the compounds (I) are usually obtained in the form of a mixture of stereo-isomers, but they can be separated into each stereo-isomer or a mixture thereof by the conventional methods such as fractional crystallization, chromatography, or the like. For example, when 2-(6,6a,7,8,9,10,10a,11-octahydro-11-oxodibenzo[b,e]thiepin-3-yl)propionic acid is subjected to fractional crystallization from ethyl acetate, there can be obtained a pair of racemic diastereomers. The racemic stereo-isomers thus obtained can be resolved into each optical isomer by a conventional resolution method using an optically active base such as cinchonidine or d- or l-α-methylbenzylamine.

The each stereo-isomer or a mixture thereof of the compounds (Ia) which is obtained by the above-mentioned methods can also be subjected to esterification or amidation reaction in order to obtain the compounds (I) wherein $R_2$ is a group other than hydroxy.

When the compounds (I) wherein $R_2$ is hydroxy are treated with an inorganic or organic base, they are converted into the corresponding salts. The inorganic or organic base includes sodium hydroxide, potassium hydroxide, calcium hydroxide, magnesium hydroxide, aluminum hydroxide, ammonium hydroxide, isopropylamine, diethylamine, ethanolamine, piperidine, or the like. The formation of the salts can be carried out in a usual manner, for example, by contacting the carboxylic acid compound (Ia) with the base as mentioned above in an appropriate solvent (e.g. water, a lower alcohol, toluene, or a mixture thereof) at a temperature of from about 0° to 100° C. The calcium or magnesium salt of the compounds (Ia) can preferably be obtained by treating the corresponding sodium or potassium salt with calcium chloride or magnesium chloride, respectively. Besides, the compounds (I) wherein $R_2$ is a basic group (e.g. pyridylmethoxy, 2-pyridylethoxy, 2-morpholinoethoxy, or 4-(2-hydroxyethyl)-1-piperazinyl)

wherein X, $R_1$ and $R_5$ are as defined above, and M is an alkali metal and Y is a halogen.

As is shown in the above reaction scheme, the compound (III) can be prepared by reacting a compound of the formula (VI) with a compound of the formula (VII) in the absence of a solvent or in a solvent having a high boiling point (e.g. dimethylformamide) at a temperature of from about 150° to about 200° C. The compound (III) wherein $R_5$ is hydrogen can alternatively be prepared by reacting a compound of the formula (VIII) with a compound of the formula (VII) in a lower alcohol (e.g. ethanol) at a temperature of about 70° to about 120° C. to obtain a compound of the formula (IX) and hydrolyzing the compound (IX) with an alkali (e.g. sodium hydroxide, potassium hydroxide) in a polar solvent having a high boiling point (e.g. diethylene glycol) at a temperature of from about 200° to about 280° C.

The compounds (VI) and (VIII) can be prepared by the processes disclosed in J. Org. Chem., 35, 3574 (1970) and Bull. Soc. Chem. France, 1966, 1315, respectively. The compounds (VII) are commercially available or can be prepared by the processes disclosed in Chem. Pharm. Bull., 26,1384 (1978), U.S. Pat. No. 4,025,528, British Pat. No. 1,543,276, etc.

The compounds of the formula (I) and pharmaceutically acceptable salts thereof have excellent anti-inflammatory, analgesic and antipyretic activities and have weak ulcerogenecity in the gastrointestinal tract and low toxicity, and hence, the compounds have a large safety margin. Thus, the compounds of the present invention are useful as an anti-inflammatory agent.

The pharmacological activities of the present compounds were tested as disclosed below. In the tests, some commercially available anti-inflammatory agents were used as a reference compound.

The compounds used in the tests are as follows:

COMPOUNDS OF THE PRESENT INVENTION

A: 2-(6,6a,7,8,9,10,10a,11-Octahydro-11-oxodibenz[b,e]oxepin-3-yl)propionic acid (cf. Example 1)

B: 6,6a,7,8,9,10,10a,11-Octahydro-11-oxodibenz[b,e]oxepin-3-acetic acid (cf. Example 3)

C: 2-(6,6a,7,8,9,10,10a,11-Octahydro-11-oxodibenz[-b,e]oxepin-2-yl)propionic acid (cf. Example 3)

D: 2-(6,6a,7,8,9,10,10a,11-Octahydro-11-oxodibenzo[b,e]thiepin-2-yl)propionic acid (cf. Example 3)

E: 6,6a,7,8,9,10,10a,11-Octahydro-11-oxodibenzo[b,e]thiepin-3-acetic acid (cf. Example 3)

F: 2-(6,6a,7,8,9,10,10a,11-Octahydro-11-oxodibenzo[b,e]thiepin-3-yl)propionic acid-A (cf. Example 15)

G: 2-(6,6a,7,8,9,10,10a,11-Octahydro-11-oxodibenzo[b,e]thiepin-3-yl)propionic acid-B (cf. Example 15)

H: Calcium 2-(6,6a,7,8,9,10,10a,11-octahydro-11-oxodibenzo[b,e]thiepin-3-yl)propionate (cf. Example 2)

I: Ethyl 2-(6,6a,7,8,9,10,10a,11-octahydro-11-oxodibenzo[b,e]thiepin-3-yl)propionate (cf. Example 4)

J: Butyl 2-(6,6a,7,8,9,10,10a,11-octahydro-11-oxodibenzo[b,e]thiepin-3-yl)propionate (cf. Example 10, Table 3)

K: Allyl 2-(6,6a,7,8,9,10,10a,11-octahydro-11-oxodibenzo[b,e]thiepin-3-yl)propionate (cf. Example 5)

L: Phenethyl 2-(6,6a,7,8,9,10,10a,11-octahydro-11-oxodibenzo[b,e]thiepin-3-yl)propionate (cf. Example 9)

M: Phenacyl 2-(6,6a,7,8,9,10,10a,11-octahydro-11-oxodibenzo[b,e]thiepin-3-yl)propionate (cf. Example 10, Table 3)

N: 2-(2-Hydroxyethoxy)ethyl 2-(6,6a,7,8,9,10,10a,11-octahydro-11-oxodibenzo[b,e]thiepin-3-yl)propionate (cf. Example 10, Table 3)

O: 2-Pyridylmethyl 2-(6,6a,7,8,9,10,10a,11-octahydro-11-oxodibenzo[b,e]thiepin-3-yl)propionate (cf. Example 10, Table 3)

P: 2-(2-Pyridyl)ethyl 2-(6,6a,7,8,9,10,10a,11-octahydro-11-oxodibenzo[b,e]thiepin-3-yl)propionate (cf. Example 7)

Q: 2-Morpholinoethyl 2-(6,6a,7,8,9,10,10a,11-octahydro-11-oxodibenzo[b,e]thiepin-3-yl)propionate (cf. Example 8)

2-(6,6a,7,8,9,10,10a,11-Octahydro-11-oxodibenzo[b,e]thiepin-3-yl)propionamide-A (cf. Example 16)

S: 2-(6,6a,7,8,9,10,10a,11-Octahydro-11-oxodibenzo[b,e]thiepin-3-yl)propionohydroxamic acid (cf. Example 13)

T: N-Carboxymethyl-2-(6,6a,7,8,9,10,10a,11-octahydro-11-oxodibenzo[b,e]thiepin-3-yl)propionamide (cf. Example 12)

REFERENCE COMPOUNDS

1: Indomethacin which is a well-known anti-inflammatory agent having potent efficacy.

2: Aspirin which is a well-known anti-inflammatory agent having mild efficacy.

TEST 1

Anti-inflammatory activity (carrageenin-induced hind paw edema in rats)

The test was carried out in a similar manner as disclosed in Proc. Soc. Exptl. Biol. Med., 111,544 (1962).

Male Wistar rats, weighing 100–300 g, were used. A 1% aqueous carrageenin solution (0.1 ml) was administered subcutaneously into the hind foot pad of rats. Two and three hours after the carrageenin injection, the paw volume was measured and the swelling rate was calculated based on the paw volume before the carrageenin injection. The inhibitory rate was determined as compared with the average swelling rate of the control group to which only vehicle was administered. The test compounds were administered orally one hour before the carrageenin injection. The results are shown in Table 1.

TABLE 1

| | | | Anti-inflammatory activity | |
| | | | Inhibitory rate (%) | |
| Test Compound | Dose (mg/kg, p.o.) | Number of rats used | Time after the carrageenin injection | |
| | | | Two hours | Three hours |
| --- | --- | --- | --- | --- |
| A | 0.5 | 10 | 23.7** | 17.4* |
| | 1 | 5 | 34.3** | 26.9** |
| | 2 | 10 | 40.5** | 32.6** |
| B | 1 | 5 | 17.8* | 7.8 |
| C | 80 | 5 | 27.9** | 23.1** |
| D | 40 | 5 | 28.6** | 24.6** |
| | 80 | 5 | 34.0** | 27.1** |
| E | 2 | 5 | 26.3** | 16.8** |
| F | 0.2 | 10 | 8.6 | 6.7 |
| | 0.4 | 10 | 14.9** | 11.6* |
| | 0.8 | 10 | 20.5** | 12.6* |
| | 1.6 | 20 | 28.4** | 20.3** |
| | 3.2 | 10 | 36.4** | 30.6** |
| G | 10 | 10 | 12.0* | 7.1 |
| | 20 | 10 | 18.3** | 11.0* |
| | 40 | 10 | 33.2** | 26.9** |
| | 80 | 5 | 32.2** | 30.2** |
| H | 1 | 5 | 31.4** | 26.2** |
| | 4 | 5 | 39.5** | 35.7** |
| I | 5 | 5 | 42.2** | 38.3** |
| J | 2 | 5 | 21.5* | 11.5 |
| | 5 | 5 | 31.8** | 26.0** |
| K | 2 | 5 | 27.0** | 22.3* |
| | 5 | 5 | 34.3** | 33.5** |
| L | 2 | 5 | 20.7** | 24.8** |
| | 5 | 5 | 44.8** | 39.1** |
| M | 5 | 10 | 33.2** | 26.6** |
| N | 2 | 5 | 15.8* | 13.2 |
| | 5 | 5 | 43.9** | 28.1** |
| O | 2 | 5 | 31.4** | 28.8** |
| | 5 | 5 | 30.8** | 30.6** |
| P | 5 | 5 | 27.6** | 25.5** |
| Q | 2 | 5 | 25.4** | 22.8** |
| | 5 | 5 | 28.9** | 22.0** |
| R | 1 | 5 | 29.3** | 24.7** |
| | 2 | 5 | 30.7** | 27.6** |
| | 4 | 5 | 38.4** | 37.7** |
| | 8 | 5 | 43.6** | 36.0** |
| S | 2 | 5 | 21.9** | 18.5** |
| | 5 | 5 | 31.5** | 29.9** |
| T | 2 | 5 | 19.9* | 15.0* |
| | 5 | 5 | 43.9** | 28.1** |
| 1 | 2 | 5 | 20.5** | 19.3* |
| | 5 | 5 | 42.4** | 36.3** |
| 2 | 20 | 10 | 14.1* | 9.0 |
| | 40 | 10 | 22.9** | 21.2** |
| | 80 | 10 | 30.8** | 25.9** |
| | 160 | 10 | 35.1** | 30.9** |

*: This means that there is significant difference as compared with the control group at $0.01 < P < 0.05$.
**: This means that there is significant difference as compared with the control group at $P < 0.01$.

As is clear from the results shown in Table 1, the compounds A, B, E, F, and H–T of the present invention showed anti-inflammatory activity comparable or superior to that of the known indomethacin. The compounds C, D and G of the present invention showed anti-inflammatory activity comparable or superior to that of the known aspirin.

Test 2

Gastrointestinal ulcerogenicity

The test was carried out in a similar manner as disclosed in Arzneim. Forsch., 19, 36 (1969).

Male Wistar rats, weighing 130–180 g, were used. After the rats were fasted for 24 hours, the test compound was orally administered one time. After 6 hours, the rats were killed and the stomach was removed. The stomach was cut open at the greater curvature and was extended on a cork plate, and the degree of stomach ulcer was observed with naked eyes. The degree of stomach ulcer was scored from 1 to 4, wherein 4 is the most severe ulcer. In Table 2, there are shown the average score of stomach ulcer in each dose and also the ratio of the number of rats having a score of stomach ulcer of 2 or more to total number of rats used.

TABLE 2

| | | Gastrointestinal ulcerogenicity |
|---|---|---|
| Test compound | Dose (mg/kg, p.o.) | Average score of stomach ulcer (Number of rats having a score of stomach ulcer of 2 or more/total number of rats used) |
| F | 16 | 1.00 (2/6) |
| | 32 | 1.00 (2/6) |
| | 64 | 1.67 (6/9) |
| H | 16 | 1.00 (1/3) |
| | 32 | 1.33 (2/3) |
| I | 8 | 0.00 (0/3) |
| | 32 | 0.33 (0/6) |
| | 64 | 1.00 (3/6) |
| J | 16 | 0.33 (0/3) |
| | 32 | 1.33 (3/6) |
| | 64 | 1.50 (3/6) |
| L | 32 | 0.56 (1/9) |
| | 64 | 0.67 (0/6) |
| O | 32 | 0.67 (2/6) |
| | 64 | 1.83 (4/6) |
| P | 32 | 0.17 (0/6) |
| | 64 | 0.50 (3/6) |
| R | 8 | 0.00 (0/3) |
| | 16 | 1.67 (4/6) |
| | 32 | 2.33 (3/3) |
| 1 | 4 | 0.50 (0/6) |
| | 8 | 1.78 (6/9) |
| | 16 | 2.56 (8/9) |
| 2 | 20 | 0.83 (0/6) |
| | 40 | 1.33 (3/6) |
| | 60 | 2.33 (5/6) |
| | 80 | 3.33 (5/6) |
| | 160 | 4.00 (6/6) |

As is clear from the results shown in Table 2, the compounds of the present invention showed far less gastrointestinal ulcerogenicity in comparison with the known indomethacin. Particularly, the compounds I, L and P showed far less gastrointestinal ulcerogenicity than the known aspirin did.

TEST 3

Acute lethal toxicity

The mortality was observed on the 7th day after single oral administration of test compounds in male Wistar rats, and the $LD_{50}$ was calculated according to the method of Litchfield and Wilcoxon.

As a result, the $LD_{50}$ of the compound L was 230 mg/kg, while that of indomethacin was 18.5 mg/kg. Thus the toxicity of the compound L is about 1/12 of that of indomethacin.

The compounds of formula (I) and pharmaceutically acceptable salts thereof are useful as anti-inflammatory agents for the treatment of various inflammatory conditions of the muscular skeletal system, skeletal joints and other tissues in mammals including humans, for example, inflammatory conditions such as rheumatism, concussion, laceration, arthritis, bone fractures, post-traumatic conditions, and peritendinitis. When these conditions include pain and fever coupled with inflammation, the compounds of the present invention are useful for the relief of these conditions as well as inflammation.

The compounds (I) and pharmaceutically acceptable salts thereof of the present invention can be administered to the patients in oral, parenteral, intrarectal, or topical route.

Dose of the compounds (I) and salts thereof may vary with the kinds of the compounds, the administration routes, the age of the patients, the kinds and severity of the diseases to be treated, or the like, but is in the range of 0.2 to 120 mg per kg of body weight per day, preferably 0.3 to 80 mg per kg of body weight per day, for humans. The dose may be divided and administered in two to several times per day.

The compounds (I) and pharmaceutically acceptable salts thereof are usually administered to patients in the form of a pharmaceutical composition which contains a non-toxic and effective amount of the compounds. The pharmaceutical composition is usually prepared by admixing the active compounds (I) or their salts with conventional pharmaceutical carrier materials which are unreactive with the active compounds (I) or their salts. Suitable examples of the carrier materials are lactose, glucose, mannitol, dextran, cyclodextrin, starch, sucrose, magnesium aluminosilicate tetrahydrate, synthetic aluminum silicate, microcrystalline cellulose, sodium carboxymethylcellulose, calcium carboxymethylcellulose, methylcellulose, gelatin, acacia, hydroxypropylcellulose, hydroxypropyl methylcellulose, polyvinylpyrrolidone, light anhydrous silicic acid, magnesium stearate, talc, tragacanth, bentonite, veegum, carboxyvinyl polymer, titanium dioxide, sorbitan fatty acid ester, sodium lauryl sulfate, cacao butter, glycerin, glycerides of saturated fatty acids, anhydrous lanolin, glycerogelatin, polysorbate, macrogol, vegetable oils, wax, cetyl alcohol, oleyl alcohol, propylene glycol, ethanol, isopropanol, water, or the like.

The pharmaceutical composition may be in the dosage form of tablets, capsules, granules, fine granules, powders, syrups, suppositories, ointments, creams, gels, injections, or the like. these preparations may be prepared by conventional methods. Liquid preparations may be prepared by dissolving or suspending the active compounds in water or other suitable vehicles, when used. Tablets may be coated in a conventional manner.

The pharmaceutical composition may contain as the active ingredient the compound (I) or its pharmaceutically acceptable salt in the ratio of 0.1% by weight or more, preferably 0.5 to 70% by weight, based upon the whole weight of the compositions. The composition may further contain one or more other therapeutically active compounds.

The present invention is illustrated more specifically by the following Examples and Reference Examples. It should be understood that the invention is not limited to these examples. The compounds were identified by elemental analysis, mass spectrum (MS), high resolution mass spectrum (HRMS), infrared (IR) spectrum, nuclear magnetic resonance (NMR) spectrum, thin layer chromatography (TLC), etc.

EXAMPLE 1

2-(6,6a,7,8,9,10,10a,11-Octahydro-11-oxodibenz[b,e]oxepin-3-yl)propionic acid and its calcium salt 2-[3-(2-Carboxycyclohexylmethyloxy)phenyl]propionic acid (14 g) was added to polyphophoric acid (80 g) and the mixture was heated with stirring for 2.5 hours in an oil bath maintained at 100° C. The reaction mixture was diluted with water and extracted with ethyl acetate. The ethyl acetate layers were washed with water, dried over anhydrous sodium sulfate, and evaporated to dryness under reduced pressure. The residue was chromatographed on silica gel, using methanol-chloroform (2:98, v/v) as an eluent, to give 2-(6,6a,7,8,9,10,10a,11-octahydro-11-oxodibenz[b,e]oxepin-3-yl)propionic acid (1.05 g) as an oil. IR $\nu_{max}^{film}$ cm$^{-1}$: 1700, 1680 (C=O). HRMS m/e: 288.1390 (M+) (Molecular weight calculated for $C_{17}H_{20}O_4$: 288.1362).

The above propionic acid compound (1.05 g) was dissolved in a solution of sodium hydroxide (0.146 g) in water (10 ml). To the solution was added a solution of calcium chloride dihydrate (0.262 g) in water (10 ml) and the resulting mixture was stirred at room temperature for one hour. Crystals precipitated were collected to give calcium 2-(6.6a,7,8,9,10,10a,11-octahydro-11-oxodibenz[b,e]oxepin-3-yl)propionate (0.20 g), m.p. 225°–235° C.

EXAMPLE 2

2-(6,6a,7,8,9,10,10a,11-Octahydro-11-oxodibenzo[b,e]-thiepin-3-yl)propionic acid and its calcium salt 2-[3-(2-Carboxycyclohexylmethylthio)phenyl]propionic acid (1.8 g) was added to polyphosphoric acid (18 g) and the mixture was heated with stirring for 2.5 hours in an oil bath maintained at 100° C. The reaction mixture was treated as in Example 1 to give 2-(6,6a,7,8,9,10,10a-11-octahydro-11-oxodibenzo[b,e]thiepin-3-yl)propionic acid (1.1 g) as an oil. IR $\nu_{max}^{film}$ cm$^{-1}$: 1700, 1670 (C=O). HRMS m/e: 304.1158 (M+) (Molecular weight calculated for $C_{17}H_{20}O_3S$: 304.1133).

The above propionic acid compound (6.08 g) was dissolved in a solution of sodium hydroxide (0.8 g) in water (100 ml). To the solution was added a solution of calcium chloride dihydrate (1.43 g) in water (20 ml) and the mixture was stirred at room temperature for one hour. Crystals precipitated were collected by filtration, washed with water and dried to give calcium 2-(6,6a,7,8,9,10,10a,11-octahydro-11-oxodibenzo[b,e]thiepin-3-yl)propionate (5.2 g), m.p. 240°–250° C.

EXAMPLE 3

The following compounds were prepared in substantially the same manner as in Examples 1 and 2, using the corresponding starting materials:

2-(6,6a,7,8,9,10,10a,11-octahydro-11-oxodibenzo[b,e]thiepin-2-yl)propionic acid, an oil, HRMS m/e: 304.1172 (M+) (Molecular weight calculated for $C_{17}H_{20}O_3S$: 304.1133), calcium 2-(6,6a,7,8,9,10,10a,11-octahydro-11-oxodibenzo[b,e]thiepin-2-yl)propionate, m.p. 210°–215° C., 6,6a,7,8,9,10,10a,11-octahydro-11-oxodibenzo[b,e]thiepin-3-acetic acid, m.p. 151°–152° C., MS m/e: 290 (M+), 2-(6,6a,7,8,9,10,10a,11-octahydro-11-oxodibenz[b,e]oxepin-2-yl)propionic acid, an oil, HRMS m/e: 288.1376 (M+) (Molecular weight calculated for $C_{17}H_{20}O_4$: 288.1362), and 6,6a,7,8,9,10,10a,11-octahydro-11-oxodibenz[b,e]oxepin-3-acetic acid, m.p. 127°–129° C., MS m/e: 274 (M+).

EXAMPLE 4

Ethyl 2-(6,6a,7,8,9,10,10a,11-octahydro-11-oxodibenzo[b,e]-thiepin-3-yl)propionate To a solution of 2-(6,6a,7,8,9,10,10a,11-octahydro-11-oxodibenzo[b,e]thiepin-3-yl)propionic acid (10 g) in ethanol (150 ml) was added 35% hydrochloric acid (10 ml) and the mixture was heated under reflux for 4 hours. Removal of the ethanol under reduced pressure afforded the title compound (10.8 g), b.p. 205° C./0.06 mmHg. IR $\nu_{max}^{film}$ cm$^{-1}$: 1720, 1660 (C=O). HRMS m/e: 332.1475 (M+) (Molecular weight calculated for $C_{19}H_{24}O_3S$: 332.1447).

EXAMPLE 5

Allyl 2-(6,6a,7,8,9,10,10a,11-octahydro-11-oxodibenzo[b,e]-thiepin-3-yl)propionate To a solution of 2-(6,6a,7,8,9,10,10a,11-octahydro-11-oxodibenzo[b,e]thiepin-3-yl)propionic acid (2.0 g) in allyl alcohol (20 ml) was added concentrated sulfuric acid (1 ml) and the mixture was heated under reflux for one hour in an oil bath maintained at 110° C. The reaction mixture was diluted with water and extracted with toluene. The toluene layers were washed with water, dried over anhydrous sodium sulfate and evaporated to dryness under reduced pressure. The residue was chromatographed on silica gel, using toluene as an eluent, to give the title compound (1.2 g) as an oil. IR $\nu_{max}^{film}$ cm$^{-1}$: 1720, 1670 (C=O). HRMS m/e: 344.1415 (Molecular weight calculated for $C_{20}H_{24}O_3S$: 344.1445).

EXAMPLE 6

Phenethyl 2-(6,6a,7,8,9,10,10a,11-octahydro-11-oxodibenz[b,e]oxepin-3-yl)propionate 2-(6,6a,7,8,9,10,10a,11-Octahydro-11-oxodibenz[b,e]oxepin-3-yl)propionic acid (1.0 g) was added to thionyl chloride (10 ml) and the mixture was refluxed with stirring for 2 hours. The excess of thionyl chloride was distilled off under reduced pressure. To the oily residue was added a solution of phenethyl alcohol (2 ml) in xylene (20 ml) and the mixture was heated under reflux for 18 hours, cooled and poured into water. The xylene layers were separated, washed with water, dried over anhydrous sodium sulfate and evaporated to dryness under reduced pressure. The residue was chromatographed on silica gel, using toluene as an eluent, to give the title compound (0.4 g) as an oil. IR $\nu_{max}^{film}$ cm$^{-1}$: 1720, 1670 (C=O). HRMS m/e: 392.2007 (M+) (Molecular weight calculated for $C_{25}H_{28}O_4$: 392.1987).

EXAMPLE 7

2-(2-Pyridyl)ethyl 2-(6,6a,7,8,9,10,10a,11-octahydro-11-oxodibenzo[b,e]-thiepin-3-yl)propionate 2-(6,6a7,8,9,10,10a,11-Octahydro-11-oxodibenzo[b,e]thiepin-3-yl)propionic acid (1.5 g) was added to thionyl chloride (15 ml) and the mixture was refluxed with stirring for 1.5 hours. The excess of thionyl chloride was distilled off under reduced pressure. The oily residue was dissolved in toluene (20 ml) and the solution was added at room temperature to a stirred solution of 2-(2-pyridyl)ethanol (1.4 g) in toluene (40 ml). The resulting mixture was stirred at room temperature for 20 hours and poured into water. The toluene layers were separated, washed with water, dried over anhydrous sodium sulfate, and evaporated to dryness under reduced pressure. The residue was chromatographed on silica gel, using chloroform as an eluent, to give the title compound (1.2 g) as an oil. IR $\nu_{max}^{film}$ cm$^{-1}$: 1720, 1670 (C=O). MS m/e: 409 (M+).

EXAMPLE 8

2-Morpholinoethyl 2-(6,6a,7,8,9,10,10a,11-octahydro-11-oxodibenzo[b,e]-thiepin-3-yl)propionate 2-(6,6a,7,8,9,10,10a,11-Octahydro-11-oxodibenzo[b,e]thiepin-3-yl)propionic acid (2.0 g), 1-(2-hydroxyethyl)morpholine (2.1 g) and p-toluenesulfonyl chloride (1.5 g) were added to dioxane (30 ml). The mixture was heated with stirring for 4 hours in an oil bath maintained at 90° C. and then evaporated to dryness under reduced pressure. The residue was dissolved in dilute hydrochloric acid. The hydrochloric acid solution was washed with toluene and extracted with chloroform. The chloroform layers were neutralized with triethylamine, washed with water and evaporated to dryness under reduced pressure. The residue was chromatographed on silica gel, using chloroform as an eluent, to give the title compound (1.5 g) as an oil. IR$\nu_{max}^{film}$ cm$^{-1}$: 1720, 1670 (C=O). HRMS m/e: 417.2017 (molecular weight calculated for $C_{23}H_{31}NO_4S$: 417.1974).

EXAMPLE 9

Phenethyl 2-(6,6a,7,8,9,10,10a,11-octahydro-11-oxodibenzo[b,e]-thiepin-3-yl)propionate 2-(6,6a,7,8,9,10,10a,11-octahydro-11-oxodibenzo[b,e]thiepin-3-yl)propionic acid (2.0 g) was dissolved in a solution of potassium hydroxide (0.41 g) in methanol (30 ml) and the solution was evaporated to dryness under reduced pressure. To the potassium salt thus obtained were added phenethyl bromide (1.4 g) and toluene (50 ml). The resulting mixture was refluxed for 16 hours in an oil bath maintained at 110° C., cooled and diluted with water. The toluene layers were separated, washed with water, dried over anhydrous sodium sulfate, and evaporated to dryness under reduced pressure. The residue was chromatographed on silica gel, using toluene as an eluent, to give the title compound (0.8 g) as an oil, b.p. 240°-242° C./0.1 mmHg. TLC [silica gel 60F$_{254}$ (Merck), CHCl$_3$]: R$_f$ 0.40. IR$\nu_{max}^{film}$ cm$^{-1}$: 1725, 1670 (C=O). HRMS m/e: 408.1747 (M+) (Molecular weight calculated for $C_{25}H_{28}O_3S$: 408.1757). NMR (CDCl$_3$) δ: 1.48 (3H, d, J=8 Hz, >CHC$\underline{H}_3$), 2.78 (1H, d-d, J = 15, 2 Hz, —SC$\underline{\text{H}}$—), 2.88 (2H, t, J=7 Hz, —C$\underline{H}_2$C$_6$H$_5$), 3.02 (1H, d-d, J = 15, 5 Hz, —SC$\underline{\text{H}}$—), 3.11 (1H, d-d-d, J=11, 11, 4 Hz, C$_{10a}$—H), 3.68 (1H, q, J=8 Hz, >C$\underline{H}$CH$_3$), 4.30 (2H, t, J=7 Hz, —OCH$_2$—), 7.04–7.80 (8H, m, aromatic H).

EXAMPLE 10

The oily ester compounds listed in Table 3 were prepared in substantially the same manner as in the above Examples, using the corresponding starting materials.

TABLE 3

| X | R | Process | M+ (High resolution mass spectrum) | Molecular formula, Molecular weight (calcd.) |
|---|---|---|---|---|
| S | -n-C$_3$H$_7$ | 5* | 346.1586 | C$_{20}$H$_{26}$O$_3$S 346.1601 |
| " | -i-C$_3$H$_7$ | " | 346.1596 | C$_{20}$H$_{26}$O$_3$S 346.1601 |
| " | -n-C$_4$H$_9$ | " | 360.1780 | C$_{21}$H$_{28}$O$_3$S 360.1760 |
| " | -i-C$_4$H$_9$ | " | 360.1753 | C$_{21}$H$_{28}$O$_3$S 360.1760 |
| " | -n-C$_5$H$_{11}$ | " | 374.1925 | C$_{22}$H$_{30}$O$_3$S 374.1916 |
| " | -i-C$_5$H$_{11}$ | " | 374.1910 | C$_{22}$H$_{30}$O$_3$S 374.1916 |
| " | -n-C$_6$H$_{13}$ | 5 | 388.2089 | C$_{23}$H$_{32}$O$_3$S 388.2072 |
| " | -n-C$_{12}$H$_{25}$ | 9 | 472.3038 | C$_{29}$H$_{44}$O$_3$S 472.3011 |
| " | —C$_6$H$_5$ | 6 | 380.1419 | C$_{23}$H$_{24}$O$_3$S 380.1444 |
| " | —CH$_2$C$_6$H$_5$ | 9 | 394.1594 | C$_{24}$H$_{26}$O$_3$S 394.1601 |
| " | —CH$_2$CH$_2$CH$_2$C$_6$H$_5$ | 6 | 422.1924 | C$_{26}$H$_{30}$O$_3$S 422.1916 |
| " | —CH$_2$CH=CHC$_6$H$_5$ | " | 420.1757 | C$_{26}$H$_{28}$O$_3$S 420.1757 |
| " | —CH$_2$COC$_6$H$_5$ | 9 | 422.1547 | C$_{25}$H$_{26}$O$_4$S 422.1550 |
| " | —CH$_2$COOC$_2$H$_5$ | " | 390.1500 | C$_{21}$H$_{26}$O$_5$S 390.1500 |
| " | —CH$_2$CH$_2$OC$_2$H$_5$ | 5 | 376.1717 | C$_{21}$H$_{28}$O$_4$S 376.1709 |
| " | —(CH$_2$CH$_2$O)$_2$H | " | 392.1655 | C$_{21}$H$_{28}$O$_5$S 392.1655 |
| " | —CH$_2$CH$_2$N(C$_2$H$_5$)$_2$ | 9 | 403.2176 | C$_{23}$H$_{33}$NO$_3$S 403.2179 |
| " | —CH$_2$CH$_2$N⟨piperidinyl⟩ | 7 | 415.2148 | C$_{24}$H$_{33}$NO$_3$S 415.2179 |
| " | —CH$_2$-(3-pyridyl) | " | 395.1526 | C$_{23}$H$_{25}$NO$_3$S 395.1553 |
| " | —CH$_2$-(4-pyridyl) | " | 395.1552 | C$_{23}$H$_{25}$NO$_3$S 395.1553 |
| " | —⟨C$_6$H$_{11}$⟩ | 5 | 386.1959 | C$_{23}$H$_{30}$O$_3$S 386.1916 |
| O | —C$_2$H$_5$ | 4 | 316.1690 | C$_{19}$H$_{24}$O$_4$ 316.1674 |
| " | -n-C$_3$H$_7$ | 5 | 330.1835 | C$_{20}$H$_{25}$O$_4$ 330.1831 |

TABLE 3-continued

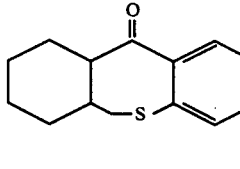

| X | R | Process | M+ (High resolution mass spectrum) | Molecular formula, Molecular weight (calcd.) |
|---|---|---|---|---|
| " | -n-C$_4$H$_9$ | 6 | 344.1978 | C$_{21}$H$_{28}$O$_4$ 344.1985 |

EXAMPLE 11

2-(6,6a,7,8,9,10,10a,11-Octahydro-11-oxodibenz[b,e]oxepin-3-yl)propionamide

A solution of 2-(6,6a,7,8,9,10,10a,11-octahydro-11-oxodibenz[b,e]oxepin-3-yl)propionic acid (1.0 g) in thionyl chloride (10 ml) was heated under reflux for 2 hours. Removal of the excess of thionyl chloride under reduced pressure afforded the acid chloride as the residue, which was dissolved in ethyl acetate (50 ml). The resulting solution was saturated with ammonia gas in an ice bath, then allowed to stand at room temperature for 30 minutes, and evaporated to dryness under reduced pressure. The oily residue was chromatographed on silica gel, using chloroform as an eluent, to give the title compound (0.6 g) as an oil. IR$\nu_{max}^{film}$ cm$^{-1}$: 3350, 3200 (NH$_2$), 1660 (C=O). HRMS m/e: 287.1487 (M+) (Molecular weight calculated for C$_{17}$H$_{21}$NO$_3$: 287.1519).

EXAMPLE 12

N-Carboxymethyl-2-(6,6a,7,8,9,10,10a,11-octahydro-11-oxodibenzo[b,e]thiepin-3-yl)propionamide A solution of 2-(6,6a,7,8,9,10,10a,11-octahydro-11-oxodibenzo[b,e]thiepin-3-yl)propionic acid (2.5 g) in thionyl chloride (15 ml) was heated under reflux for 2 hours. The excess of thionyl chloride was distilled off under reduced pressure to give the acid chloride as the residue, to which was added in an ice bath a solution of glycine (19 g) and sodium hydroxide (10 g) in water (20 ml). The resulting mixture was stirred for 30 minutes in an ice bath, then acidified with hydrochloric acid and extracted with chloroform. The chloroform layers were washed with water, dried over anhydrous sodium sulfate and evaporated to dryness under reduced pressure. The oily residue was chromatographed on silica gel, using methanol-chloroform (5:95, v/v) as an eluent, to give the title compound (1.2 g) as an oil. IR$\nu_{max}^{KBr}$ cm$^{-1}$: 1650 (C=O). HRMS m/e: 361.1368 (M+) (Molecular weight calculated for C$_{19}$H$_{23}$NO$_4$S: 361.1348).

EXAMPLE 13

2-(6,6a,7,8,9,10,10a,11-Octahydro-11-oxodibenzo[b,e]thiepin-3-yl)propionohydroxamic acid 2-(6,6a,7,8,9,10,10a,11-Octahydro-11-oxodibenzo[b,e]thiepin-3-yl)propionic acid (2.4 g) was added to thionyl chloride (15 ml) and the mixture was refluxed for 2 hours in an oil bath maintained at 120° C. The excess of thionyl chloride was distilled off under reduced pressure to give the acid chloride as the residue, which was dissolved in toluene (50 ml). To the solution was added in an ice bath a hydroxylamine solution prepared from hydroxylamine hydrochloride (5.5 g), sodium (1.8 g) and ethanol (70 ml). The mixture was stirred for 30 minutes in an ice bath and evaporated to dryness under reduced pressure. The residue was diluted with water and extracted with chloroform. The chloroform layers were washed with water, dried over anhydrous sodium sulfate and evaporated to dryness under reduced pressure. The residue was chromatographed on silica gel, using methanol-chloroform (3:97) as an eluent, to give the title compound (2.0 g) as an oil. IR$\nu_{max}^{film}$ cm$^{-1}$: 3300 (OH, NH), 1650 (C=O). MS m/e: 319 (M+).

EXAMPLE 14

The oily amide compounds listed in Table 4 were prepared in substantially the same manner as in Examples 11 to 13, using the corresponding starting materials.

TABLE 4

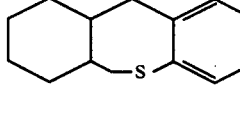

| N$<^{R_3}_{R_4}$ | M+ (High resolution mass spectrum) | Molecular formula, Molecular weight (calcd.) |
|---|---|---|
| —NHCH$_3$ | 317.1422 | C$_{18}$H$_{23}$NO$_2$S 317.1448 |
| —N(CH$_3$)$_2$ | 331.1599 | C$_{19}$H$_{25}$NO$_2$S 331.1605 |
| —NHCH$_2$C$_6$H$_5$ | 393.1729 | C$_{24}$H$_{27}$NO$_2$S 398.1761 |
| 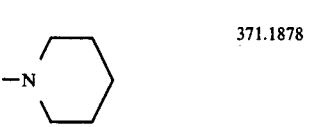 | 371.1878 | C$_{22}$H$_{29}$NO$_2$S 371.1918 |
|  | 373.1689 | C$_{21}$H$_{27}$NO$_3$S 378.1711 |
|  | 386.1989 | C$_{22}$H$_{30}$N$_2$O$_2$S 386.2026 |
| —NHCH$_2$CH$_2$OH | 347.1590 | C$_{19}$H$_{25}$NO$_3$S 347.1555 |
| 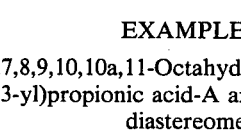 | 416.2102 | C$_{23}$H$_{32}$N$_2$O$_3$S 416.2132 |

EXAMPLE 15

2-(6,6a,7,8,9,10,10a,11-Octahydro-11-oxodibenzo[b,e]thiepin-3-yl)propionic acid-A and -B (Isolation of two diastereomers)

To oily 2-(6,6a,7,8,9,10,10a,11-octahydro-11-oxodibenzo[b,e]thiepin-3-yl)propionic acid (39 g) prepared by the method described in Example 2 was added ethyl acetate (25 ml) for crystallization. Crystals precipitated were collected by filtration and recrystallized repeatedly from ethyl acetate to give 2-(6,6a,7,8,9,10,-10a,11-octahydro-11-oxodibenzo[b,e]thiepin-3-yl)propionic acid-B (9 g; hereinafter referred to as the Racemate B), m.p. 179°–181° C. IR$\nu_{max}^{KBr}$ cm$^{-1}$: 1705, 1680 (C=O). MS m/e: 304 (M+). NMR (CDCl$_3$) δ: 1.50 (3H, d, J=8 Hz, >CHC$\underline{H}_3$), 2.78 (1H, d-d, J = 15, 2 Hz, —SC$\underline{H}$—), 3.03 (1H, d-d, J = 15, 5 Hz, —SC$\underline{H}$—), 3.12 (1H, d-d-d, J=11, 11, 4 Hz, C$_{10a}$—H), 3.71 (1H, q, J=8 Hz, >C$\underline{H}$CH$_3$), 7.13–7.83 (3H, m, aromatic H). The J value between C$_{10a}$ proton and C$_{6a}$ proton was 11.0 Hz. This suggests the trans configuration for this product.

Mother liquors obtained by the above crystallization procedures were evaporated to dryness under reduced pressure. The residue was crystallized by adding a proper amount of ethyl acetate. Crystals precipitated were collected by filtration and recrystallized repeatedly from ethyl acetate to give 2-(6,6a,7,8,9,10,10a,11-octahydro-11-oxodibenzo[b,e]thiepin-3-yl)propionic acid-A (5.5 g; hereinafter referred to as the Racemate A), m.p. 161°–162° C. IR$\nu_{max}^{KBr}$ cm$^{-1}$: 1690, 1670 (C=O). MS m/e: 304 (M+). The NMR spectrum of this product was the same as that of the Racemate B.

EXAMPLE 16

2-(6,6a,7,8,9,10,10a,11-Octahydro-11-oxodibenzo[b,e]-thiepin-3-yl)propionamide-A (Isolation of one diastereomer)

To oily 2-(6,6a,7,8,9,10,10a,11-octahydro-11-oxodibenzo[b,e]thiepin-3-yl)propionamide (18 g) prepared in substantially the same manner as in Example 11 was added ethyl acetate (20 ml) for crystallization. Crystals precipitated were collected by filtration and recrystallized repeatedly from ethyl acetate to give the title compound (6.0 g), m.p. 189°–192° C. IR$\nu_{max}^{KBr}$ cm$^{-1}$: 3340, 3180 (NH$_2$), 1650 (C=O). MS m/e: 303 (M+).

This product was shown to be identical with the amide compound prepared from the Racemate A of Example 15 by the method described in Example 11 by the mixed melting point and comparison of various spectra.

EXAMPLE 17

2-(6,6a,7,8,9,10,10a,11-Octahydro-11-oxodibenzo[b,e]-thiepin-3-yl)propionamide-B The oily title compound was prepared in substantially the same manner as in Example 11, using the Racemate B of Example 15. IR$\nu_{max}^{film}$ cm$^{-1}$: 3320, 3170 (NH), 1650 (C=O). HRMS m/e: 303.1319 (M+) (Molecular weight calculated for C$_{17}$H$_{21}$NO$_2$S: 303.1293).

EXAMPLE 18

Separation of the diastereomers of 2-(6,6a,7,8,9,10,10a,11-octahydro-11-oxodibenzo[b,e]-thiepin-3-yl)propionic acid The 2-(6,6a,7,8,9,10,10a,11-octahydro-11-oxodibenzo[b,e]thiepin-3-yl)propionic acid prepared by the method described in Example 2 was submitted to high performance liquid chromatography to separate each diastereomers. The apparatus used as ALC/GPC 204 made by Waters Co..

The analytical conditions were as follows:
Column: μBondapak C$_{18}$, 4 mm ID×300 mm,
mobile phase: 1% NaHCO$_3$-dioxane-CH$_3$CN (77:20:3, v/v),
flow rate: 2.5 ml/min.,
detector: ultraviolet absorption (254 nm),
column temperature: room temperature,
sample: 5 μl (1 mg/ml MeOH).

The chromatogram obtained was shown in the accompanying FIGURE. Peaks 1 and 2 were identical with those of the Racemate B and Racemate A of Example 15, respectively. Peak 3 was assumed to be that of another couple of diastereomers, the Racemate C and Racemate D.

The starting materials used in Examples 1 and 2 were prepared as follows.

REFERENCE EXAMPLE 1

2-[3-(2-Carboxycyclohexylmethylthio)phenyl]propionic acid

Sodium ethylate prepared from sodium (0.23 g) and ethanol (10 ml) was added to ethyl 2-(3-mercaptophenyl)propionate (2.10 g) and the mixture was stirred for a while. Thereto was added trans-2-(chloromethyl)-cyclohexanenitrile (1.58 g) and the resulting mixture was refluxed for 5 hours in an oil bath maintained at 100° C. The reaction mixture was evaporated to dryness under reduced pressure and to the residue was added toluene. After removal of the insoluble material by filtration, the solvent was distilled off under reduced pressure. The residue was chromatographed on silica gel, using chloroform as an eluent, to give ethyl 2-[3-(2-cyanocyclohexylmethylthio)phenyl]propionate (2.6 g) as an oil. IR$\nu_{max}^{film}$ cm$^{-1}$: 2230 (C≡N), 1720 (C=O). MS m/e: 331 (M+).

The above ester compound (2.6 g) was added to a solution of potassium hydroxide (2.6 g) in water (5 ml) and diethylene glycol (8 ml) and the mixture was heated with stirring for 5.5 hours in an oil bath maintained at 250° C. The reaction mixture was poured into water, acidified with hydrochloric acid and extracted with ethyl acetate. The ethyl acetate layers were washed with water, dried over anhydrous sodium sulfate and evaporated to dryness under reduced pressure to give the title compound (2.5 g) as an oil. IR$\nu_{max}^{film}$ cm$^{-1}$: 1700 (C=O). MS m/e: 322 (M+).

REFERENCE EXAMPLE 2

2-[3-(2-Carboxycyclohexylmethylthio)phenyl]propionic acid

To 2-(3-mercaptophenyl)propionic acid (2.7 g) were added cis-2-(hydroxymethyl)cyclohexanecarboxylic acid lactone (2.5 g), potassium carbonate (2.5 g) and dimethylformamide (25 ml). The mixture was heated with stirring for 3 hours in an oil bath maintained at 170° C. and evaporated to dryness under reduced pressure. The residue was dissolved in water, acidified with hydrochloric acid and extracted with ethyl acetate. The ethyl acetate layers were washed with water, dried over anhydrous sodium sulfate and evaporated to dryness under reduced pressure to give the title compound (4.6 g) as an oil. IR $\nu_{max}^{film}$ cm$^{-1}$: 1700 (C=O). MS m/e: 322 (M+).

REFERENCE EXAMPLE 3

2-[3-(2-Carboxycyclohexylmethyloxy)phenyl]propionic acid

To 2-(3-hydroxyphenyl)propionic acid (19.2 g) were added cis-2-(hydroxymethyl)cyclohexanecarboxylic acid lactone (19.5 g), potassium carbonate (19.2 g) and dimethylformamide (200 ml). The mixture was heated with stirring for 3 hours in an oil bath maintained at 170° C. The reaction mixture was treated in substantially the same manner as in Reference Example 2. There was obtained the title compound (14 g) as an oil. IR $\nu_{max}^{film}$ cm$^{-1}$: 1700 (C=O). MS m/e: 306 (M+).

The following oily compounds were prepared in substantially the same manner as in Reference Examples 1 to 3, using the corresponding starting materials:
ethyl 2-[4-(2-cyanocyclohexylmethylthio)phenyl]propionate, MS m/e: 331 (M+),
ethyl 2-[4-(2-cyanocyclohexylmethyloxy)phenyl]propionate, MS m/e: 315 (M+),
2-[4-(2-carboxycyclohexylmethylthio)phenyl]propionic acid, MS m/e: 322 (M+),
2-[4-(2-carboxycyclohexylmethyloxy)phenyl]propionic acid, MS m/e: 306 (M+),
3-(2-carboxycyclohexylmethylthio)phenylacetic acid, MS m/e: 308 (M+), and
3-(2-carboxycyclohexylmethyloxy)phenylacetic acid, MS m/e: 292 (M+).

EXAMPLE 19

|  | per 1,000 tablets |
| --- | --- |
| Calcium 2-(6,6a,7,8,9,10,10a,11-octahydro-11-oxodibenzo[b,e]-thiepin-3-yl)propionate | 25 g |
| Corn starch | 28 g |
| Lactose | 60 g |
| Microcrystalline cellulose | 30 g |
| Hydroxypropylcellulose | 5 g |
| Light anhydrous silicic acid | 1 g |
| Magnesium stearate | 1 g |

The above components were blended, granulated and made into tablets by a conventional method to form 1,000 tablets each weighing 150 mg.

EXAMPLE 20

|  | per 1,000 capsules |
| --- | --- |
| Phenethyl 2-(6,6a,7,8,9,10,10a,11-octahydro-11-oxodibenzo[b,e]-thiepin-3-yl)propionate | 50 g |
| Corn starch | 55 g |
| Lactose | 24 g |
| Microcrystalline cellulose | 120 g |
| Talc | 0.5 g |
| Magnesium stearate | 0.5 g |

The above components were blended, granulated and filled into 1,000 capsules by a conventional method.

EXAMPLE 21

|  | per 1,000 capsules |
| --- | --- |
| Phenethyl 2-(6,6a,7,8,9,10,10a,11-octahydro-11-oxodibenzo[b,e]-thiepin-3-yl)propionate | 50 g |
| Vegetable oil | 150 g |

The above components were blended and filled into 1,000 soft capsules by a conventional method.

What is claimed is:

1. A compound of the formula

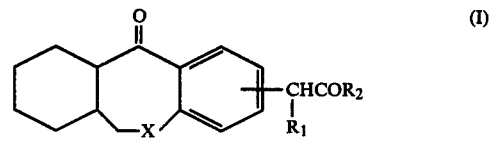

wherein X is oxygen or sulfur; R$_1$ is hydrogen or a lower alkyl; R$_2$ is hydroxy, an alkoxy, an alkenyloxy, a cycloalkyloxy, an aryloxy, a substituted aryloxy, an aryl-lower alkoxy, a substituted aryl-lower alkoxy, an aryl-lower alkenyloxy, a substituted aryl-lower alkenyloxy, an ω-disubstituted amino-lower alkoxy, a lower alkoxy-carbonyl-lower alkoxy, a lower alkoxy-lower alkoxy, a hydroxy-lower alkoxy-lower alkoxy, an acyl-lower alkoxy, or a group

wherein R$_3$ is hydrogen, hydroxy, a lower alkyl, an aryl-lower alkyl, a hydroxy-lower alkyl, or a carboxy-lower alkyl, R$_4$ is hydrogen, a lower alkyl, or a hydroxy-lower alkyl, or the R$_3$ and R$_4$ may combine together with the nitrogen atom to which they are joined to form a 5- or 6-membered heterocyclic group which may contain one additional hetero-atom selected from the group consisting of nitrogen, oxygen and sulfur, said heterocyclic group being optionally substituted with a lower alkyl or a hydroxy-lower alkyl, and in the foregoing definition the substituent in the substituted aryl is a halogen, a lower alkyl or a lower alkoxy and the disubstituent in the w-disubstituted amino is two alkyl or a 5- or 6-membered cyclic amino; and the group —CH(R$_1$)COR$_2$ is joined to the carbon atom at the 2- or 3-position, or a pharmaceutically acceptable salt thereof.

2. A compound according to claim 1, wherein R$_1$ is hydrogen or methyl and the group —CH(R$_1$)COR$_2$ is joined to the carbon atom at 3-position, or a pharmaceutically acceptable salt thereof.

3. A compound according to claim 2, wherein R$_1$ is methyl, or a pharmaceutically acceptable salt thereof.

4. A compound according to claim 1, 2 or 3, wherein X is oxygen, or a pharmaceutically acceptable salt thereof.

5. A compound according to claim 1, 2 or 3, wherein X is sulfur, or a pharmaceutically acceptable salt thereof.

6. A compound of the formula (II):

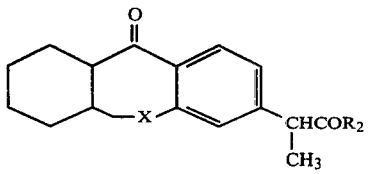

(II)

wherein X is oxygen or sulfur; $R_2$ is hydroxy, an alkoxy having 1 to 6 carbon atoms, an alkenyloxy having 3 to 5 carbon atoms, cyclohexyloxy, phenyloxy, a phenyl-lower alkoxy, a pyridyl-lower alkoxy, a phenyl-lower alkenyloxy, an ω-disubstituted amino-lower alkoxy, a lower alkoxy-carbonyl-lower alkoxy, a lower alkoxy-lower alkoxy, a hydroxy-lower alkoxy-lower alkoxy, a benzoyl-lower alkoxy, amino, hydroxyamino, a hydroxy-lower alkylamino, or a carboxy-lower alkylamino, or a pharmaceutically acceptable salt thereof.

7. The compound of claim 6, wherein X is oxygen or sulfur and $R_2$ is hydroxy, an alkoxy having 1 to 4 carbon atoms, phenethyloxy, 2-pyridylmethoxy, 2-(2-pyridyl)ethoxy, or amino, or a pharmaceutically acceptable salt thereof.

8. A compound according to claim 6 or 7, wherein X is oxygen, or a pharmaceutically acceptable salt thereof.

9. A compound according to claim 6 or 7, wherein X is sulfur, or a pharmaceutically acceptable salt thereof.

10. The compound of claim 6, wherein X is oxygen and $R_2$ is hydroxy, or a pharmaceutically acceptable salt thereof.

11. The compound of claim 6, wherein X is sulfur and $R_2$ is hydroxy, or a pharmaceutically acceptable salt thereof.

12. The compound of claim 6, wherein X is sulfur and $R_2$ is ethoxy.

13. The compound of claim 6, wherein X is sulfur and $R_2$ is butoxy.

14. The compound of claim 6, wherein X is sulfur and $R_2$ is phenethyloxy.

15. The compound of claim 6, wherein X is sulfur and $R_2$ is amino.

16. A pharmaceutical composition comprising an effective amount of a compound of the formula (I) as set forth in claim 1, or a pharmaceutically acceptable salt thereof and a pharmaceutically acceptable carrier.

17. A pharmaceutical composition comprising an effective amount of the compound of claim 6, or a pharmaceutically acceptable salt thereof.

18. A pharmaceutical composition comprising an effective amount of a compound or a pharmaceutically acceptable salt thereof as set forth in claim 11, and a pharmaceutically acceptable carrier.

19. A pharmaceutical composition comprising an effective amount of a compound as set forth in claim 12, and a pharmaceutically acceptable carrier.

20. A pharmaceutical composition comprising an effective amount of a compound as set forth in claim 13, and a pharmaceutically acceptable carrier.

21. A pharmaceutical composition comprising an effective amount of a compound as set forth in claim 14, and a pharmaceutically acceptable carrier.

22. A pharmaceutical composition comprising an effective amount of a compound as set forth in claim 15, and a pharmaceutically acceptable carrier.

* * * * *